United States Patent
Wada et al.

(10) Patent No.: US 6,432,075 B1
(45) Date of Patent: *Aug. 13, 2002

(54) APPLICATOR FOR TAMPONS

(75) Inventors: Mitsuhiro Wada; Ayami Suga, both of Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/708,843

(22) Filed: Nov. 8, 2000

(30) Foreign Application Priority Data

Nov. 19, 1999 (JP) ............................... 11-329621

(51) Int. Cl.[7] ................................................. A61F 13/20
(52) U.S. Cl. ........................................................ 604/15
(58) Field of Search ............................ 604/11–18, 904, 604/57–60, 285–288, 311

(56) References Cited

U.S. PATENT DOCUMENTS

| | | | | |
|---|---|---|---|---|
| 3,934,584 A | * | 1/1976 | Corio ............................ | 604/59 |
| D250,663 S | * | 12/1978 | Koch et al. ...................... | 604/15 |
| 4,428,370 A | * | 1/1984 | Keely ............................ | 604/15 |
| 4,536,178 A | * | 8/1985 | Lichstein et al. ............... | 604/15 |
| 4,900,299 A | * | 2/1990 | Webb ............................ | 604/15 |
| 5,792,096 A | * | 8/1998 | Rentmeester .................... | 604/14 |

* cited by examiner

*Primary Examiner*—Dennis Ruhl
(74) *Attorney, Agent, or Firm*—Darby & Darby

(57) ABSTRACT

Provided is an applicator for a tampon including an outer cylinder having a large diameter portion for fitting a tampon therein, a small diameter portion provided on the side of a rear end of the outer cylinder and having a smaller diameter than that of the large diameter portion; and a plurality of valves provided on the side of a leading end of the outer cylinder. The valves are converged to have a curved face portion to be diametrically gradually reduced toward the leading end of the outer cylinder, and a push-out member is movably inserted into the small diameter portion of the outer cylinder. A ratio A/B is at most 0.8, when an inflection point for the boundary between the maximum diameter portion of the large diameter portion and the curved face portion is designated by Z, a radius of the outer face at the inflection point Z is designated by A, and the axial length from the inflection point Z to the leading end of the curved face portion is designated by B. A ratio L/W is within a range of 1.0 to 2.0, when the width size of root ends of the valves is designated by W and the length of the valves is designated by L.

6 Claims, 3 Drawing Sheets

APPLICATOR FOR TAMPONS

BACKGROUND OF THE INVENTION

1. Field of the Invention

The present invention relates to an applicator for a tampon to be employed when a sanitary tampon is to be inserted into a human body.

2. Description of the Related Art

The applicator for the sanitary tampon is constructed to include an outer cylinder for fitting the tampon therein, and an inner cylinder inserted into the outer cylinder and protruding rearwardly from the rear end of the outer cylinder. A take-out cord extending from the tampon, is led out of the outer cylinder through the inner cylinder and protruded rearwardly from a rear end of the inner cylinder.

When the tampon is to be employed, the outer cylinder is inserted into a vaginal cavity, and the inner cylinder is pushed to push the tampon out of the outer cylinder. Then, the tampon is inserted into the vaginal cavity while expanding a number of deformable valves at the leading end of the outer cylinder.

Some of the existing applicators are formed to have an outer cylinder and an inner cylinder which are made of paper. In recent years, however, an outer cylinder injection-molded of a synthetic resin has been employed so that it may have a smooth surface and may be smoothly inserted into the vaginal cavity.

FIG. 4 is a partial side elevation showing an ordinary shape of the leading end portion of an outer cylinder 30 of a conventional applicator.

The outer cylinder 30 of the conventional applicator is constructed to include a cylindrical large diameter portion 30a, and a curved face portion 30b is formed on the side of the leading portion with respect to the large diameter portion 30a through an inflection point Zo. The curved face portion 30b is formed into a generally semispherical shape which has a radial center located at the center O of the section extending through the inflection point Zo. Therefore, a ratio Ao/Bo is about 1, if the radius of the outer periphery at the inflection point Zo is designated by Ao and the axial length from the inflection point Zo to the leading end of the curved face portion 30b is designated by Bo.

In the curved face portion 30b, there are formed a plurality of valves 31 extending toward the leading end and arranged in a petal shape. These valves 31 are deformed to converge toward the leading end at the curvature of the curved face portion 30b.

However, in the shape of the leading portion of the outer cylinder 30 of the conventional applicator for the sanitary tampon as shown in FIG. 4, the large diameter portion 30a has the cylindrical shape, and the semispherical curved face portion 30b is formed at the leading end of the large diameter portion 30a. Accordingly, upon using the applicator, this shape exerts restrictions on the reduction of the resistance to the insertion into the vaginal cavity.

Therefore, the resistance to the insertion into the vaginal cavity could be reduced, if the leading end of the outer cylinder was formed not into the semispherical shape but into the shape in which the diameter is gradually reduced toward the leading portion, that is, in which the ratio Ao/Bo is smaller than 1.

However, if the leading end of the outer cylinder is formed into the shape in which the diameter is gradually reduced, the valves 31 have to be accordingly elongated in the axial direction. If the axial length size of the valves is thus enlarged at the leading portion of the outer cylinder, the shape of the leading ends of the valves is not stabilized but may be deformed to open the leading ends of the valves when the valves are thermally deformed into the curved face shape with the tampon being fitted in the outer cylinder. If the valves are opened, the leading portion of the outer cylinder may give an unnecessary resistance to the human body or may damage the body when the leading portion of the outer cylinder is inserted into the vaginal cavity.

In order to use the valves each having a long axial length and to stabilize the shape of the thermally deformed valves, it is necessary to thicken the outer cylinder itself or to injection-mold a highly hard resin. With the increased thickness, however, the amount of resin to be employed increases to cause a problem that the environment is adversely affected by the dumped resin. On the other hand, if the hard resin is employed, the values become hard to increase the contact resistance to the body. Furthermore, the fluidity of the resin in the injection mold is reduced to easily cause the defective molding of the valves and the like.

SUMMARY OF THE INVENTION

The invention has an object to provide an applicator for a tampon in which valves provided at the leading portion can be easily molded and can be prevented from opening at the leading ends, when the leading portion of an outer cylinder thereof is shaped to be easily inserted into a vaginal cavity.

According to an aspect of the invention, an applicator for a tampon may comprise: an outer cylinder including a large diameter portion for fitting a tampon therein, a small diameter portion provided on the side of a rear end of the outer cylinder and having a smaller diameter than that of the large diameter portion, and a plurality of valves provided on the side of a leading end of the outer cylinder, the valves being converged to have a curved face portion to be diametrically gradually reduced toward the leading end of the outer cylinder; and a push-out member movably inserted into the small diameter portion of the outer cylinder, wherein a ratio A/B is at most 0.8, when an inflection point for the boundary between the maximum diameter portion of the large diameter portion and the curved face portion is designated by Z, a radius of the outer face at the inflection point Z is designated by A, and the axial length from the inflection point Z to the leading end of the curved face portion is designated by B, and wherein a ratio L/W is within a range of 1.0 to 2.0, when the width size of root ends of the valves is designated by W and the length of the valves is designated by L.

According to the invention, the curved face portion of the leading portion is shaped such that the ratio A/B is at most 0.8, so that it is possible to reduce the resistance to the insertion into the vaginal cavity in comparison with the conventional outer cylinder having the semispherical curved face portion as shown in FIG. 4.

In this case, the valves will be elongated in the axial direction of the outer cylinder. However, by shaping the valves to have the ratio L/W within the range of 1.0 to 2.0, i.e., by securing a large width W of the root end with respect to the length L, the force for holding the resin distortion upon thermally deforming the valves into a curved face shape can be intensified to restrain the restoration so that the valves can be suppressed from being opened at their leading portions.

On the other hand, the root ends of the valves are located substantially at the same position of the inflection point Z.

In the curved face portion, moreover, it is preferred that the curved face portion has two curvatures, and the curvature at the leading end portions of the valves is larger than that at the root ends of the valves.

In this case, it is preferred that the axial length Y of the valve portions having the larger curvature is one half or less than the axial length B from the inflection point Z to the leading end of the curved face portion.

In the leading portion of the large diameter portion of the outer cylinder, the leading end portions of the valves are deformed at the large curvature, so that the plastic deformation of the leading end portions of the valves can be enlarged to further suppress opening of the leading ends of the valves. Since the leading end portions of the valves are formed to have the large curvature, they are prevented, when inserted into the human body, from abutting against the body, thereby giving no uncomfortable feeling to the body.

DESCRIPTION OF THE PREFERRED EMBODIMENT

Figure 1:
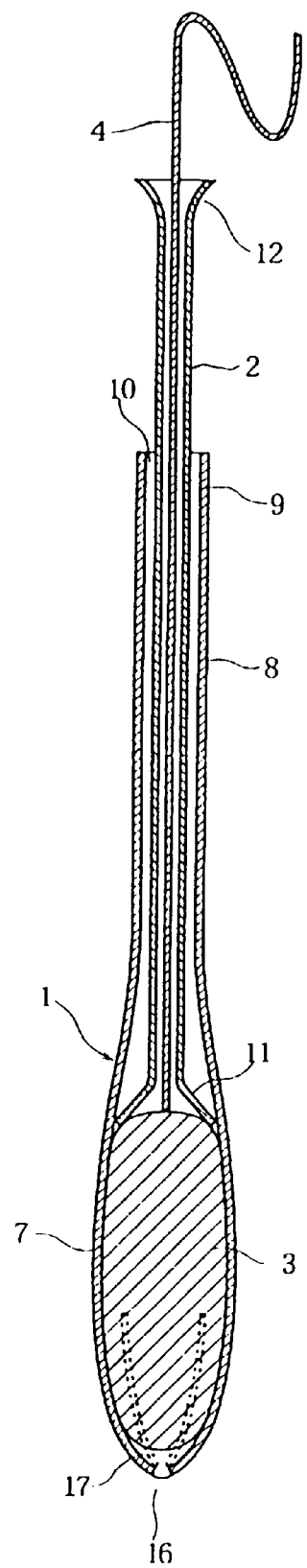
FIG. 1 is a longitudinal section showing the state in which a tampon is fitted in an applicator according to the invention.
Figure 2A:
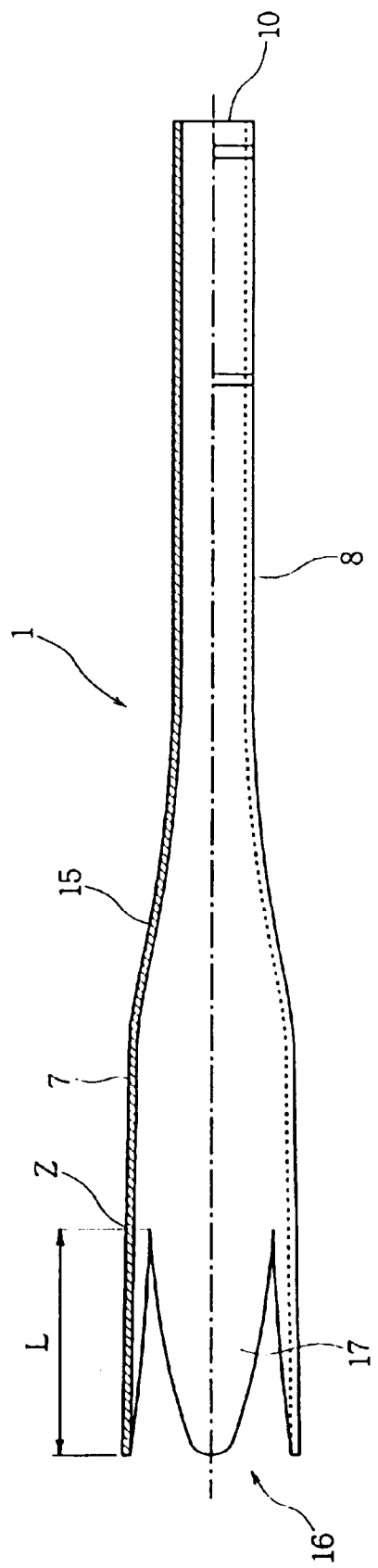
FIG. 2A is a side elevation including a sectional half and showing the state in which an outer cylinder is injection-molded.
Figure 2B:
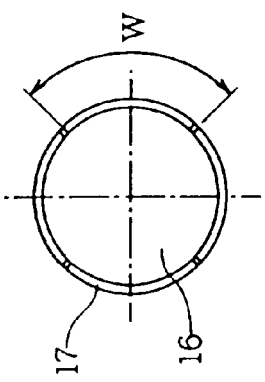
FIG. 2B is an end view of a leading portion of the outer cylinder.
Figure 3:
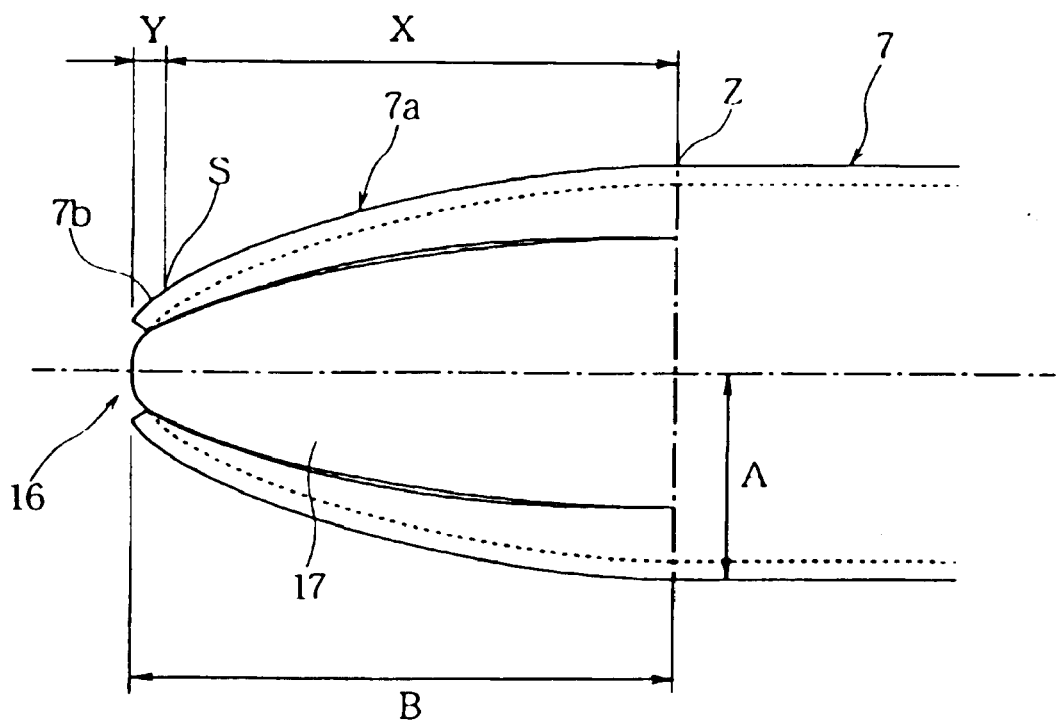
FIG. 3 is an enlarged side elevation showing the state in which valves are curved.

FIG. 1 is a longitudinal section showing the state in which a tampon is fitted in an applicator according to the invention; FIG. 2A is a side elevation showing the state in which an outer cylinder is injection-molded; FIG. 2B is an end view of a leading portion of the outer cylinder; and FIG. 3 is an enlarged side elevation showing the state in which valves are curved.

The applicator for a tampon, as shown in FIG. 1, is constructed to include an outer cylinder 1 and an inner cylinder 2 (or a push-out member). In the leading portion of the outer cylinder 1, there is fitted a tampon 3 which is formed by compress-molding absorptive fibers such as cotton. To this tampon 3, there is connected a take-out cord 4 which is extended rearwardly from the inside of the outer cylinder 1 through the inner cylinder 2.

The outer cylinder 1 is injection-molded of a thermoplastic resin such as PE (polyethylene) or PP (polypropylene). The outer cylinder 1 thus injection-molded has a smooth surface to give little uncomfortable feeling when it comes into contact with the human body. The thermoplastic resin is preferably exemplified by the LDPE (i.e., low density polyethylene) when the outer cylinder 1 is injection-molded, so that the resin may flow without stagnation in the mold thereby to provide a smooth surface and a thickness as small as possible. The thickness of the outer cylinder 1 to be formed by the injection-molding is within a range of 0.6 mm to 1.0 mm.

The inner cylinder 2 provided as a push-out member for pushing out the tampon 3 is formed of an extruded material by extrusion-molding the thermoplastic resin such as PE, PP or PET (i.e., polyethylene terephthalate) into a cylindrical shape (e.g., a straw shape or a pipe shape). More preferably, the extruded thermoplastic resin is oriented in the axial direction. The extruded material thus extrusion-molded and axially oriented is improved in the axial orientation so that its axial buckling strength is enhanced. Even if the thickness is made so small as 0.4 mm or less (up to about 0.1 mm) and the internal diameter is made so small as 7 mm or less (up to about 3 mm), the inner cylinder 2 retains a sufficient buckling strength. Accordingly, the inner cylinder 2 is hardly buckled or not folded, when the inner cylinder 2 is pushed to push out the tampon 3 from the outer cylinder 1 upon use.

The inner cylinder 2 is movably inserted into a small diameter portion 8 of the outer cylinder 1 and has a push portion 11 at a leading end thereof. This push portion 11 is diverged to push the tampon 3 easily from its rear end and to prevent the inner cylinder 2 from being withdrawn from a rear end 9 of the outer cylinder 1. At the rear end of the inner cylinder 2, there is also formed a diverging portion 12. Accordingly, the inner cylinder 2 can be easily pushed at the rear end thereof with a finger of the user, although the inner cylinder 2 has a smaller diameter.

FIG. 2A shows the state in which the outer cylinder 1 is injection-molded. The outer cylinder 1 immediately after injection-molded has a cylindrical shape, in which a large diameter portion 7 has a constant external diameter. Between this large diameter portion 7 and the small diameter portion 8 on the rear side, there is formed an inflection plane 15 at which the external diameter gradually changes. Between the large diameter portion 7 and the small diameter portion 8, however, there may be formed a step, across which the external diameter of the outer cylinder 1 may be abruptly changed.

In the leading end of the large diameter portion 7, there is opened a protruding mouth 16, around which there are formed four valves 17 in a petal shape. The valves 17 are converged to have their width sizes reducing gradually toward the leading end of the outer cylinder 1 so that they have a generally conical shape at their leading ends. The valves 17 have a length L, as taken in the axial direction of the outer cylinder 1. Furthermore, as shown in the end view of the leading portion of the outer cylinder of FIG. 2B, the valves 17 have a width W at root ends thereof.

In the assembling process of the applicator, the push portion 11 is firstly expanded at the leading end of the inner cylinder 2. The rear end of the inner cylinder 2 is inserted from the protruding mouth 16 of the outer cylinder 1 and is guided through the small diameter portion 8 until it is protruded rearwardly from an opening 10 in the rear end 9 of the outer cylinder 1. After this, the diverging portion 12 is formed at the rear end of the inner cylinder 2 protruding rearwardly from the opening 10.

The tampon 3 is inserted from the protruding mouth 16 into the large diameter portion 7 of the outer cylinder 1. At this time, the take-out cord 4 is pulled out through the inner cylinder 2 rearwardly from the rear end of the inner cylinder 2.

After the tampon 3 is inserted into the large diameter portion 7 of the outer cylinder 1, a heated press die is applied to the leading portion of the large diameter portion 7 of the outer cylinder 1 to deform the valves 17 thermally. As a result, the valves 17 are deformed to converge toward the leading end so that a curved face portion 7a is formed on the outer cylinder 1 on the side of the leading portion with respect to the large diameter portion 7, as shown in FIG. 3. The curved face portion 7a has a length B, as taken in the axial direction of the outer cylinder 1. The valves 17 having the length L as shown in FIG. 2A, are curved and deformed to form the curved face portion 7a so that the ratio of B to L is B<L. In the shown embodiment, more specifically, the boundary between generally cylindrical large diameter portion 7 and the curved face portion 7a has a inflection point Z (or a first inflection point Z), which is located at a position substantially identical to the root ends of the valves 17 in the axial direction of the outer cylinder 1.

In the curved face portion 7a, a leading end portion 7b within a predetermined length range (i.e., a length range Y in the axial direction of the outer cylinder 1) from the leading end to the root end side of the valves 17 is formed to have a larger curvature than that of the curved face portion 7a closer to the root end side than the leading end portions 7b. Namely, in this outer cylinder 1, there are formed the inflection point Z, at which the large diameter portion 7 leads into the curved face portion 7a, and a second inflection point S which is located in front of the inflection point Z and leads into the leading end portions 7b. Furthermore, the leading end portion 7b in the range Y has a larger curvature than that of the curved face portion 7a in the range X on the root end side.

Figure 4:
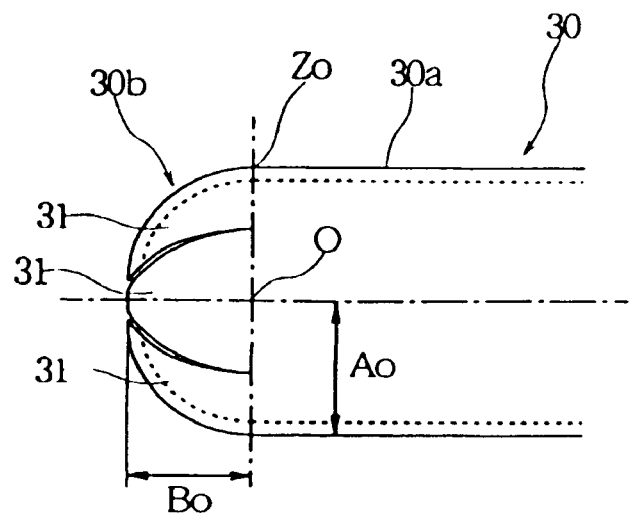
FIG. 4 is an enlarged side elevation showing the leading end shape of a conventional applicator.

With the large diameter portion 7 shown in FIG. 3, when the outer face of the large diameter portion 7 at the inflection point Z has a radius A and the axial length from the inflection point Z to the leading end of the outer cylinder 1 is B, a ratio A/B is at most 0.8, or preferably at most 0.6, Therefore, the curved face portion 7a is formed so as to converge toward the leading portion and is more slender than the curved semispherical face portion 30b of the conventional applicator shown in FIG. 4. Accordingly, it is possible to reduce the resistance which might otherwise be felt when the leading portion of the outer cylinder 1 is inserted into the vaginal cavity.

Moreover, a ratio L/W between the length L of the valve 17 and the width W of the root end is set within a range of 1.0 to 2.0. As a result, when the valves 17 are deformed to conform to the converging curved face portion 7a, the plastically deformed curved state can be easily kept to make the valves 17 reluctant to open at their leading ends. When the valves 17 of the outer cylinder 1 are deformed from the state shown in FIG. 2A, the heated die is pushed to heat and deform the synthetic resin of the valves 17 at a temperature over the glass transition temperature, and then the resin is cooled to have its orientation changed into the curved state. If the ratio L/W is at least 2.0 at this time, the valves 17 are elongated so much as to reduce the amount of the resin being oriented in the curved state. Therefore, it is hard to keep the curved state so that the valves 17 easily restore their original shape after shaped and tend to open at the leading ends by the external force.

At the tip of the curved face portion 7a, as shown in FIG. 3, the curvature of the leading end portions 7b is made larger than that of the curved face portion 7a in the range X. As a result, the curved deformation of the leading ends of the valves 17 can be enlarged to suppress the leading ends from opening. On the other hand, at the leading end portions 7b, the valves 17 converge at their leading ends with the large curvature so that their leading ends are prevented from abutting against the human body when inserted into the vaginal cavity.

The leading end portions 7b are preferably formed locally at the tips of the valves 17. Therefore, in the axial sizes of the outer cylinder 1, the relation between the length Y of the leading end portions 7b and the length X of the curved face portion 7a close to the root end side is preferably Y<X, i.e., the ratio Y/B is at most 0.5, or more preferably the ratio Y/B is at most 0.3.

There were molded the applicators which had the leading end shapes of the sizes of Example 1, Example 2, Example 3, and Comparative Example 1 and Comparative Example 2, as shown in the following Table 1.

The employed resin was LDPE (i.e., low density polyethylene) having a density of 0.92 g/cm$^3$ and an MFR (i.e., melt flow rate) of 48. This resin was injection-molded to form the outer cylinder 1 having a shape similar to that shown in FIG. 2A.

Evaluations

Injection-Moldability:

The outer cylinder having a shape similar to that shown in FIG. 2A was injection-molded, and the shape of the leading portions of the valves were observed. The outer cylinders were judged as defective moldings, as indicated by "X", if their leading ends were cut out or burred.

Opening of Valves at Leading End:

The injection-molded outer cylinder was heated at its leading end with the die so that the valves were curved to form the curved face portion, and was left for one week in the oven of 40° C. The opening of the leading ends of the valves was observed. The valves were judged to be defective, as indicated by "X", if their leading ends were deformed to outwardly open by 2 mm or more than those before left.

Push-out Feasibility (or Pushability):

The tampon was fitted in the applicator and was actually employed by the consumer. The resistance at the time when the tampon was pushed out by pushing the inner cylinder was tested. The tampon was judged to be defective, as indicated by "X", if the user felt it difficult to push out the tampon.

TABLE 1

|  | Thickness (mm) | External Diameter at Z (mm) | Outer Periphery at Z (mm) | Number of Petals | Root End Width (W) of Petals (mm) | Length (L) of Petals (mm) | L/W | Injection Moldability | Opening of Leading End | Pushability |
| --- | --- | --- | --- | --- | --- | --- | --- | --- | --- | --- |
| Example 1 | 0.60 | φ 12.9 | 40.5 | 4 | 10.12 | 17.3 | 1.7 | ○ | ○ | ○ |
| Example 2 | 0.60 | φ 14.0 | 43.9 | 4 | 10.90 | 18.8 | 1.7 | ○ | ○ | ○ |
| Example 3 | 0.60 | φ 12.9 | 40.5 | 6 | 6.75 | 8.8 | 1.3 | ○ | ○ | ○ |
| Com. Ex. 1 | 0.60 | φ 12.9 | 40.5 | 3 | 13.30 | 8.8 | 0.66 | ○ | ○ | x |
| Com. Ex. 2 | 0.60 | φ 12.9 | 40.5 | 6 | 6.75 | 15.5 | 2.3 | x | x | ○ |

The evaluation results have revealed that the range of L/W from 1.0 to 2.0 was excellent, as in Example 1, Example 2 and Example 3, in the injection moldability, in the opening of the leading end of the valves, and in the push-out feasibility. Comparative Example 1 had the ratio L/W of 0.66 so that the leading portion was not converged to make it difficult to push the tampon. On the other hand, Comparative Example 2 had the ratio L/W over 2.0 so that the valves had a poor injection moldability and easily opened at their leading end.

According to the invention set forth above, the curved face portion at the leading portion of the large diameter portion of the applicator is converged to be easily inserted into the vaginal cavity. With such a shape, the valves are prevented from being cut out or burred when injection-molded, and are hardly opened when curved. Furthermore, by enlarging the curvature of the leading end portions of the valves, it becomes easy to suppress opening of the leading ends of the valves.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. An applicator for a tampon, comprising:

an outer cylinder including forward and rearward ends, a first portion for fitting the tampon therein formed on a side of the forward end, and a second portion formed on a side of the rearward end and having a smaller diameter than that of said first portion, a push-out member movably inserted into said second portion of said outer cylinder, and a plurality of valves provided with the forward end of said outer cylinder, each valve being converged to have a curved face portion to be diametrically gradually reduced and define a leading end, wherein a ratio of a radius of an outer face at an inflection point of a boundary between a maximum diameter portion of said first diameter portion and said curved face portion to an axial length of the outer face from the inflection point to the leading end of said curved face portion is at most 0.8; and wherein a ratio of a length of said valves to a width of root ends of said valves is 1.0 to 2.0.

2. An applicator for a tampon as set forth in claim 1, wherein the root ends of said valves are located substantially at the inflection point.

3. An applicator for a tampon as set forth in claim 1, wherein said curved face portion has two curvature radii, and one curvature radius at the leading ends of said curved face portions is smaller than the other curvature radius at the root ends of said valves.

4. An applicator for a tampon as set forth in claim 3, wherein an axial length of said valves having a smaller curvature radius is one half or less than the axial length of the outer face from the inflection point to the leading end of said curved face portion.

5. An applicator for a tampon, comprising:

an outer cylinder including forward and rearward ends, a first portion for fitting a tampon therein formed on a side of the forward end, and a second portion formed on a side of the rearward end and having a reduced diameter relative to said first portion, a push-out member movably inserted into said second portion of said outer cylinder, and a plurality of valves provided with the forward end of said outer cylinder, each having a root end, a curved face portion to be diametrically gradually reduced, a leading end, a first inflection point at the root end of said valve and a second inflection point adjacent to the leading end of said valves, a curvature radius for said first inflection point being larger than a curvature radius for said second inflection point, wherein a ratio of a radius of an outer radius at said first inflection point to an axial length of said curved face from said first inflection point to the leading end of said curved face portion is at most 0.8; and wherein a ratio of a length of said valves to a width of said root ends of said valves is 1.0 to 2.0.

6. An applicator for a tampon comprising:

an outer cylinder made of a thermoplastic resin and including forward and rearward ends, a first portion for accommodating the tampon therein formed on a side of the forward end, and a second portion formed on a side of the rearward end and having a reduced diameter relative to said first portion;

a push-out member movably inserted into said second portion of said outer cylinder;

a plurality of valves provided with the forward end of said outer cylinder, each valve being converged to have a curved face portion to be diametrically gradually reduced and define a leading end;

wherein a ratio of an outer radius at an inflection point of a boundary between a maximum diameter portion of said first portion and said curved face portion to an axial length of said curved face portion from the inflection point to the leading end of said curved face portion is at most 0.8; and wherein a ratio of a length of said valves to a width of root ends of said valves is 1.0 to 2.0.

* * * * *